(12) United States Patent
Stoklund

(10) Patent No.: US 11,406,469 B2
(45) Date of Patent: Aug. 9, 2022

(54) NO TOUCH STERILE MEDICAL DEVICE PACKAGING

(71) Applicant: Ole Stoklund, Lausanne (CH)

(72) Inventor: Ole Stoklund, Lausanne (CH)

(73) Assignee: GETSET SURGICAL SA

( * ) Notice: Subject to any disclaimer, the term of this patent is extended or adjusted under 35 U.S.C. 154(b) by 0 days.

(21) Appl. No.: 16/897,470

(22) Filed: Jun. 10, 2020

(65) Prior Publication Data
US 2021/0386498 A1 Dec. 16, 2021

(51) Int. Cl.
*A61B 50/30* (2016.01)
*A61B 50/00* (2016.01)

(52) U.S. Cl.
CPC ...... *A61B 50/30* (2016.02); *A61B 2050/0066* (2016.02); *A61B 2050/3006* (2016.02); *A61B 2050/3011* (2016.02)

(58) Field of Classification Search
CPC ............ A61B 50/30; A61B 2050/0066; A61B 2050/3006; A61B 2050/3011; B65D 25/10; B65D 25/107
USPC .................................................. 206/804, 438
See application file for complete search history.

(56) References Cited

U.S. PATENT DOCUMENTS

| | | | |
|---|---|---|---|
| 4,206,844 A | 6/1980 | Thukamoto et al. | |
| 4,216,860 A | 8/1980 | Heimann | |
| 4,339,885 A * | 7/1982 | Brown | G09F 3/00 40/309 |
| 4,542,825 A | 9/1985 | Thomas et al. | |
| 4,697,703 A | 10/1987 | Will | |
| 4,750,619 A * | 6/1988 | Cohen | A61F 2/0095 206/363 |
| 4,856,648 A | 8/1989 | Krueger | |
| 5,176,258 A | 1/1993 | Antal | |
| 5,312,254 A | 5/1994 | Rosenlicht | |
| 5,542,539 A | 8/1996 | Early | |
| 5,690,222 A | 11/1997 | Peters | |
| 6,883,268 B2 * | 4/2005 | Fraser | A01K 97/22 206/315.11 |
| 8,006,839 B2 * | 8/2011 | Hafner | A61B 50/30 206/363 |
| 9,265,579 B2 | 2/2016 | Richart | |

(Continued)

FOREIGN PATENT DOCUMENTS

| | | |
|---|---|---|
| EP | 1842505 | 10/2007 |
| FR | 2656792 | 7/1991 |

(Continued)

*Primary Examiner* — Steven A. Reynolds
(74) *Attorney, Agent, or Firm* — David Meibos; Maywood IP Law

(57) ABSTRACT

A packaging assembly may retain a sterile medical device for use in a surgical setting, such as an orthopedic implant or instrument. The packaging assembly may have a first packaging component and a second packaging component. The first packaging component and the second packaging component may be attachable to each other to define a first interior space containing the medical device. The first packaging component may have a first retention feature that defines a first interior receptacle shaped to receive at least part of the medical device such that a user can manually grip the medical device through the first retention feature. The first interior space may be manually opened by a user grasping the medical device through the first retention feature.

24 Claims, 6 Drawing Sheets

(56) References Cited

U.S. PATENT DOCUMENTS

| | | |
|---|---|---|
| D775,351 S | 12/2016 | Agarwal et al. |
| 9,585,727 B2 | 3/2017 | Richart |
| 9,592,098 B2 | 3/2017 | Richart |
| 9,750,579 B2 | 9/2017 | Richart |
| 9,790,015 B2 | 10/2017 | Richart |
| 9,872,754 B2 | 1/2018 | Tuechsen et al. |
| 10,130,439 B2 | 11/2018 | Richart |
| 10,327,857 B2 | 6/2019 | Richart et al. |
| 10,383,695 B2 | 8/2019 | Richart |
| 2005/0033430 A1 | 2/2005 | Powers et al. |
| 2006/0243616 A1 | 11/2006 | Caron |
| 2008/0230423 A1 | 9/2008 | Loeffler et al. |
| 2013/0000262 A1 | 1/2013 | Richart |
| 2014/0042050 A1 | 2/2014 | Richart et al. |
| 2016/0106507 A1 | 4/2016 | Richart |
| 2016/0287293 A1 | 10/2016 | Karas et al. |
| 2017/0095308 A1 | 4/2017 | Roesler et al. |
| 2018/0178963 A1 | 6/2018 | Richart |
| 2019/0133707 A1 | 5/2019 | Richart |
| 2019/0192250 A1 | 6/2019 | Richart |
| 2019/0314133 A1 | 10/2019 | Richart |
| 2019/0321123 A1 | 10/2019 | Richart et al. |
| 2020/0010244 A1 | 1/2020 | Richart |

FOREIGN PATENT DOCUMENTS

| | | |
|---|---|---|
| WO | WO2009007891 | 1/2009 |
| WO | WO2019030451 | 2/2019 |
| WO | WO2019220067 | 11/2019 |

* cited by examiner

NO TOUCH STERILE MEDICAL DEVICE PACKAGING

TECHNICAL FIELD

The present disclosure relates to packaging systems, and more specifically, packaging for keeping medical devices, such as surgical implants and instruments, in a sterile condition until use.

BACKGROUND

In many cases, medical implants or instruments must be sterilized, and stored in a sterile condition, until they are to be used. Many types of packaging are used to provide a hermetic seal to maintain such a sterile condition. However, significant drawbacks are present with many known packaging types. Some packaging assemblies are bulky, heavy, expensive, and/or difficult to open. Many do not have any mechanism whereby the user can easily keep the medical device from contamination after the packaging has been opened and before surgical use. In many instances, sterile packaging is opened outside the sterile field, and a practitioner with contaminated fingers or gloves may inadvertently touch the medical device, rendering it unusable.

SUMMARY

The various systems and methods of the present disclosure have been developed in response to the present state of the art, and in particular, in response to the problems and needs in the art that have not yet been fully solved by currently available technology.

In some embodiments, a packaging assembly may be provided, for retaining a medical device, such as an implant or instrument, for use in a surgical setting. The packaging assembly may have a first packaging component and a second packaging component. The first packaging component and the second packaging component may be attachable to each other to define a first interior space containing the medical device. The first interior space may be sealed from ambient space. The first packaging component may have a first retention feature that defines a first interior receptacle shaped to receive at least part of the medical device such that a user can manually grip the medical device through the first retention feature.

The first retention feature may further define a first recess proximate the medical device. The first recess may be shaped to receive at least part of a user's hand.

The medical device may have a first end and a second end. The first recess may have a substantially annular shape that defines the first interior receptacle. The first interior receptacle may be shaped to receive the first medical device end.

The second packaging component may have a second retention feature that defines a second interior receptacle that receives the second medical device end.

The medical device may have a first end and a second end. The second packaging component may have a first end at which the second packaging component is secured to the first packaging component, and a second end defining a base capable of supporting the packaging assembly in an upright orientation, with the first packaging component over the second packaging component, and the medical device upright with the first end over the second end.

The first packaging component may be detachable from the second packaging component in response to manual exertion of a detachment force exerted by a user gripping the medical device through the first retention feature.

The packaging assembly may further have a third packaging component securable to the second packaging component to define a second interior space between the first interior space and an ambient space outside the packaging assembly.

The packaging assembly may further have a cap securable to the first packaging component. The cap may define a seal that seals the first interior space from ambient space.

The medical device may have a first medical device end and a second medical device end. The second packaging component may have a second retention feature that defines a second interior receptacle. With the first packaging component and the second packaging component attached to each other to define a first interior space, the first medical device end may reside in the first interior receptacle and the second medical device end may reside in the second interior receptacle.

In some embodiments, a method may be used to remove a medical device, for use during a surgical procedure, from a packaging assembly. The method may include grasping a first packaging component of the packaging assembly by grasping the medical device through a first retention feature of the first packaging component, with the medical device residing in an interior space between the first packaging component and a second packaging component of the packaging assembly. The method may further include grasping the second packaging component and, with the medical device grasped through the first retention feature, exerting a detachment force to detach the first packaging component from the second packaging component to access a first interior space between.

The first retention feature may further define a first interior receptacle. Grasping the medical device through the first retention feature may include grasping the medical device with at least part of the medical device residing in the first interior receptacle.

The first retention feature may further have a first recess. Grasping the medical device through the first retention feature may further include inserting at least part of a user's hand into the first recess.

The medical device may have a first device end and a second device end. The first recess may have a substantially annular shape that defines the first interior receptacle. Grasping the device through the first retention feature may further include grasping the first device end with the first device end residing in the first interior receptacle.

The second packaging component may have a second retention feature that defines a second interior receptacle. Grasping the second packaging component may include grasping the second packaging component with the second device end residing in the second interior receptacle.

The method may further include grasping a third packaging component secured to the second packaging component to define a second interior space between the first interior space and an ambient space outside the packaging assembly, and exerting a second detachment force to break a second seal between the third packaging component and the second packaging component to access the second interior space.

The method may further include grasping a cap secured to the second packaging component, and exerting a second detachment force to detach the cap from the first packaging component and break a seal between the cap and the first packaging component.

The medical device may have a first device end and a second device end. The second packaging component may have a second retention feature that defines a second interior receptacle. Grasping the second packaging component of the packaging assembly may include grasping the second packaging component of the packaging assembly with the second device end residing in the second interior receptacle.

According to some embodiments, a system may include a medical device for use during a surgical procedure, which may be an implant or instrument. The medical device may have a first device end and a second device end. The system may further include a packaging assembly with a first packaging component with a first retention feature that defines a first interior receptacle in which the first device end resides, and a recess sized to receive at least part of a hand of a user and shaped to permit the user to compress the first interior receptacle against the first end of the device. The packaging assembly may further include a second packaging component with a second retention feature that defines a second interior receptacle in which the second device end resides. The first packaging component and the second packaging component may be attachable to each other to define a first interior space containing the medical device in a sealed condition.

The system may further have a third packaging component securable to the second packaging component to define a second interior space between the first interior space and an ambient space outside the packaging assembly.

The first packaging component may be detachable from the second packaging component in response to manual exertion of a detachment force exerted by a user gripping the medical device through the first retention feature.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

FIGS. 2A, 2B, and 2C are a plan view, an alternative side elevation section view, and a perspective view, respectively, of the packaging assembly of FIG. 1.

FIG. 3 is a side elevation, exploded view of the packaging assembly of FIG. 1.

Figure 1:
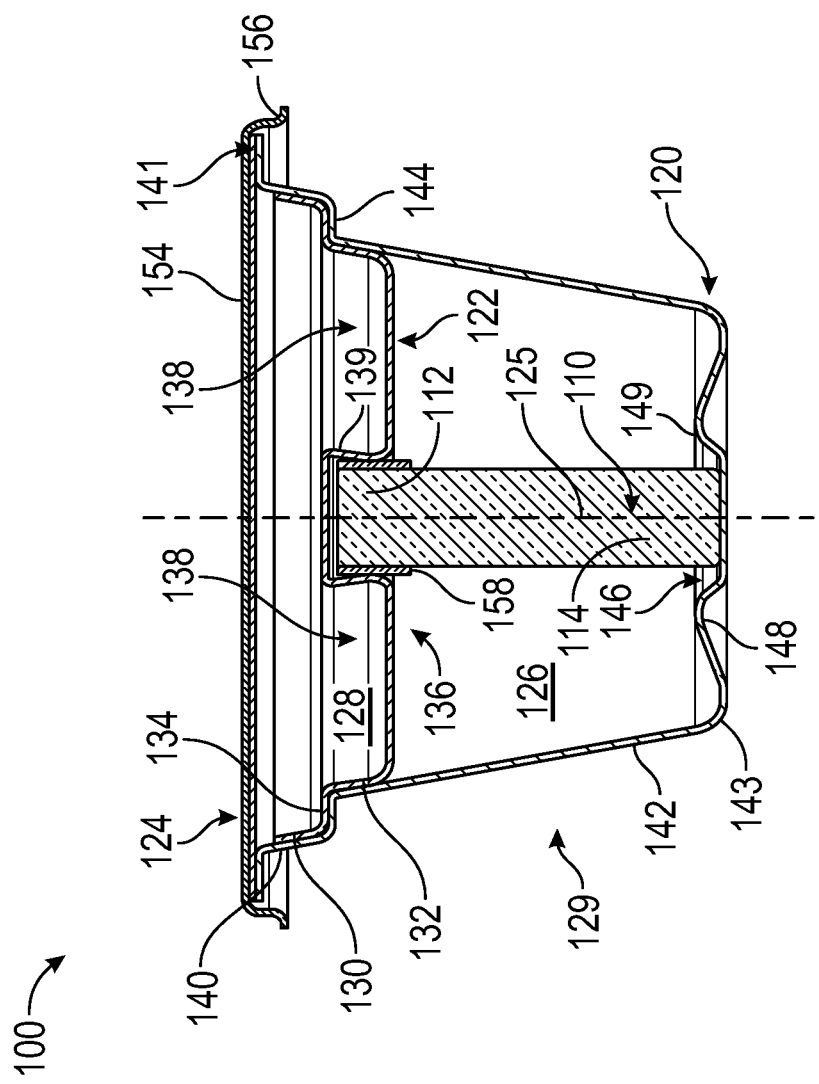
Referring to FIGS. 1, 2A, 2B, 2C, and 3, a side elevation, section view of a packaging assembly containing a medical device, according to one embodiment.
Figure 2B:
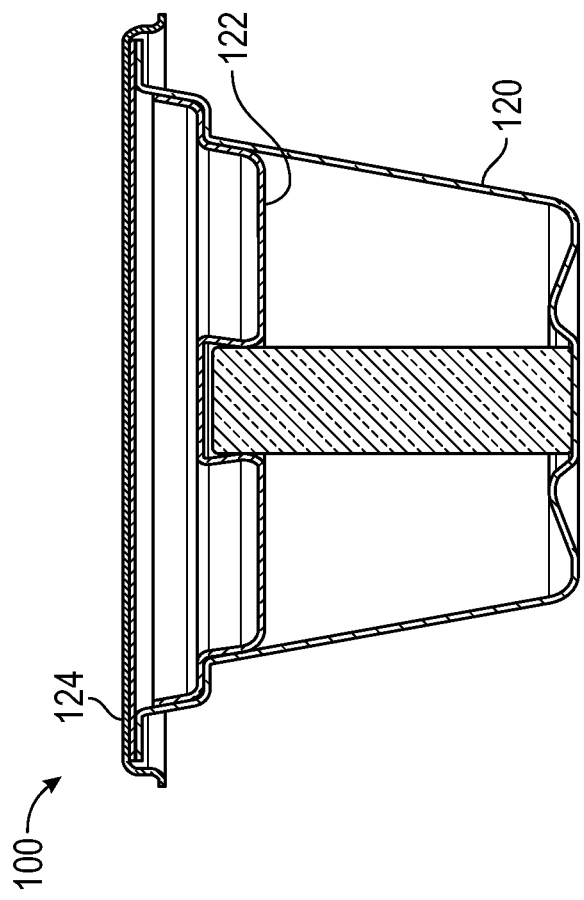
Figure 2A:
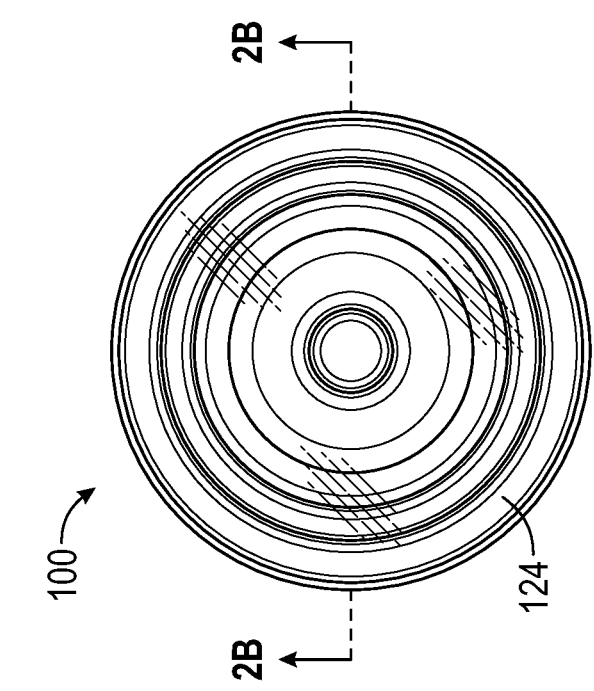
Figure 2C:
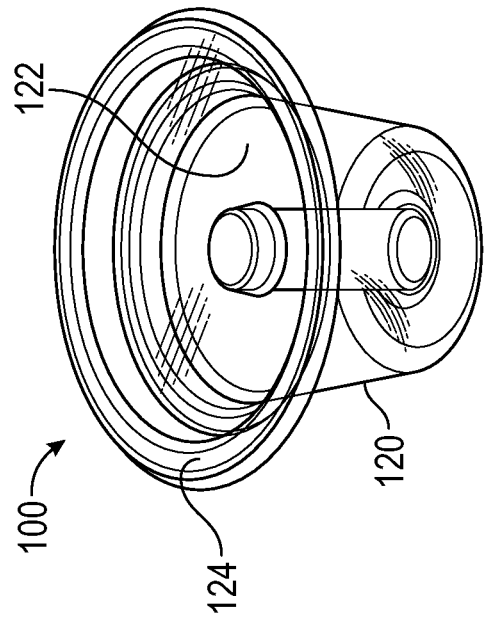
Figure 3:
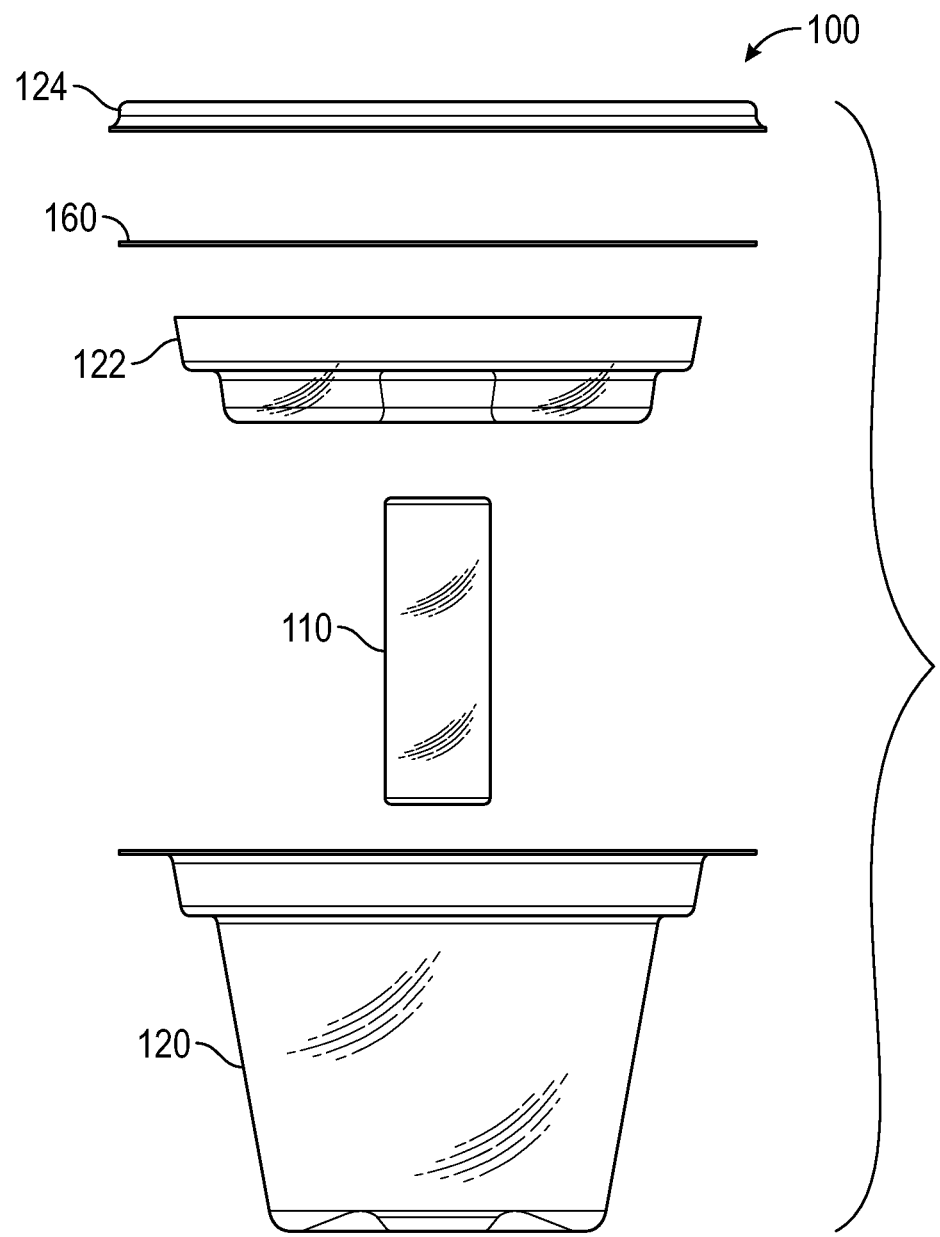

It is to be understood that the drawings are for purposes of illustrating the concepts of the disclosure and are not to scale. Furthermore, the drawings illustrate exemplary embodiments and do not represent limitations to the scope of the disclosure.

DETAILED DESCRIPTION

Exemplary embodiments of the invention will be best understood by reference to the drawings, wherein like parts are designated by like numerals throughout. It will be readily understood that the components of the invention, as generally described and illustrated in the Figures herein, could be arranged and designed in a wide variety of different configurations. Thus, the following more detailed description of the embodiments of the apparatus, system, and method, as represented in FIGS. 1 through 5C, is not intended to limit the scope of the invention, as claimed in this or any other application claiming priority to this application, but is merely representative exemplary of exemplary embodiments of the invention.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature. The phrase "manually touching" refers to touching an object with hands or other body parts, without regard as to whether the hands or other body parts are gloved or otherwise protected. "Without manually touching" refers to an action that is carried out on an object without touching the object with hands or other body parts, without regard as to whether the hands or other body parts are gloved or otherwise protected.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Referring to FIGS. 1, 2A, 2B, 2C, and 3, a side elevation, section view, a plan view, an alternative side elevation section view, a perspective view, and a side elevation, exploded view show a packaging assembly 100, according to one embodiment. The packaging assembly 100 may be used to contain a medical device 110, which may be any type of device that is usable in a surgical environment, such as a surgical implant or instrument. For example, the medical device 110 may be a bone screw, a spinal stabilization rod, an intervertebral implant, a stent, or any other implantable device known in the medical arts. In alternative embodiments, the medical device 110 may be an instrument retained in sterile condition in the packaging assembly 100.

Figure 4:
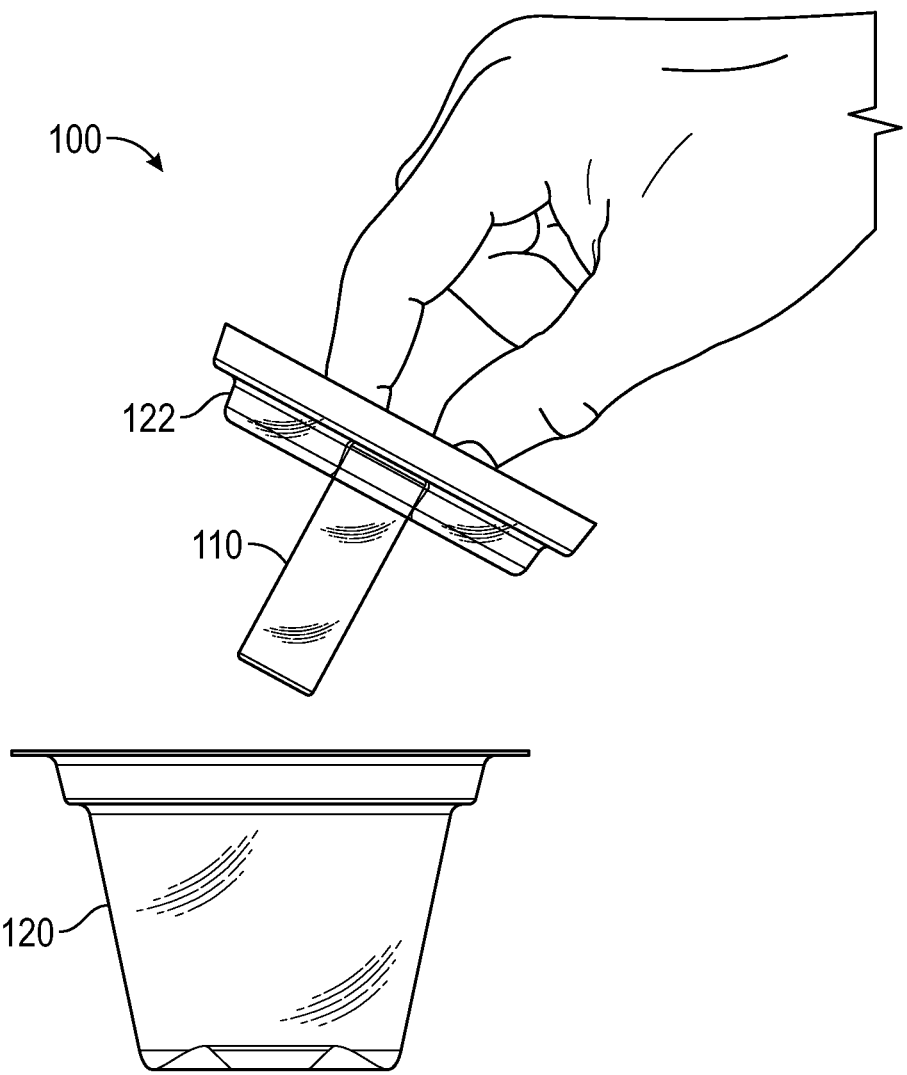
FIG. 4 is a side elevation view of the packaging assembly of FIG. 1, with the first packaging component detached from the second packaging component to permit removal of the medical device.

FIG. 4 is a side elevation view of the packaging assembly 100, with the packaging assembly 100 open to permit removal of the medical device 110. In some embodiments, the medical device 110 may already be packaged in another form of sterile packaging prior to insertion into the packaging assembly 100. The retaining features of the packaging assembly 100 can then engage the other sterile packaging. In such a situation, the packaging assembly 100 may provide a second sterile barrier to further protect the medical device 110 from contamination.

In the exemplary embodiment of FIG. 1, the medical device 110 is shown as a spinal stabilization rod, and may thus have a generally cylindrical, elongated shape. The medical device 110 may have a first end 112 and a second end 114. The medical device 110 may be used for posterior vertebral stabilization, in connection with a series of pedicle screws with polyaxially-adjustable rod receivers (not shown).

In order to avoid introduction of infection in the surgical site, it may be desirable for the medical device 110 to remain sterile until it is needed. Accordingly, in addition to safely storing the medical device 110, the packaging assembly 100 may maintain the medical device 110 in a sterile environment until it is time to use the medical device 110 surgically. Optionally, the packaging assembly 100 may enable an operator to remove the medical device 110 from the packaging assembly 100 without requiring the operator to manually touch the medical device 110, thus preserving the sterile state of the medical device 110. The medical device 110 may then, in its sterile state, be transferred directly to the sterile field or the surgical site for use.

According to some embodiments, the packaging assembly 100 may have a first packaging component 120, a second packaging component 122, and a third packaging component 124. In some embodiments, the first packaging component 120, the second packaging component 122, and the third packaging component 124 may each be generally radially symmetrical about an axis 125 of the first packaging component 120. The second packaging component 122 may seat securely into the first packaging component 120.

In some embodiments, the first packaging component 120 and the second packaging component 122 may be seated together in a manner that provides a seal. However, in alternative embodiments, no seal may be provided by the interface between the first packaging component 120 and the second packaging component 122. Rather, a cap 160 may be sealed onto the first packaging component 120 to create the sterile seal. The cap 160 may be a Tyvek layer or the like. In other embodiments, the packaging assembly 100 may provide multiple seals, for example, with a first seal between the first packaging component 120 and the second packaging component 122, and a second seal between the first packaging component 120 and the cap 160.

The first packaging component 120 and the second packaging component 122 may be complementarily shaped such that they can be easily secured together to define a first interior space 126 between them. Further, the third packaging component 124 may be complementarily shaped with the first packaging component 120 and/or the second packaging component 122 such that the third packaging component 124 can be secured to the first packaging component 120 and/or the second packaging component 122. In some embodiments, the third packaging component 124 may be secured to the first packaging component 120 to define a seal. This may be done in addition to, or in the alternative to, seals between the first packaging component 120 and the third packaging component 124 and/or the cap 160. Attachment of the third packaging component 124 to the first packaging component 120 may define a second interior space 128 generally between the second packaging component 122 and the third packaging component 124. The medical device 110 may reside in the first interior space 126. The second interior space 128 may, if sealed, provide a supplemental seal between the first interior space 126 and an ambient space 129 outside the packaging assembly 100.

The second packaging component 122 may have a first end 130, a second end 132, a shoulder 134, and a retention feature 136. The first end 130 may be generally open toward the third packaging component 124, such that the second interior space 128 is accessible through the first end 130. The second interior space 128 may generally reside within the first packaging component 120. The second end 132 may be closed to provide a barrier, and in some embodiments a seal, between the first interior space 126 and the second interior space 128. In embodiments in which the first packaging component 120 is sealed to the second packaging component 122, the shoulder 134 may provide a generally annular surface that can readily be attached to and/or sealed against the second packaging component 122, as will be described subsequently.

The retention feature 136 may retain the first end 112 of the medical device 110 in such a manner that the first end 112 can be gripped through the second packaging component 122. More particularly, the retention feature 136 may have a recess 138 with a generally annular shape that surrounds the first end 112, to define a second interior receptacle 139 that receives the first end 112. The recess 138 may be sized such that an operator, such as a surgeon or other clinician, can insert the tips of his or her fingers and/or thumb into the recess 138 and grip the first end 112 of the medical device 110 through the second packaging component 122. This may facilitate removal of the medical device 110 from the packaging assembly 100 without requiring the clinician to touch the medical device 110 with his or her fingers or gloves.

The generally annular shape of the recess 138 is merely exemplary. In alternative embodiments, a wide variety of other shapes may be used. According to one alternative embodiment (not shown), multiple distinct recesses may be used for different digits of the user. For example, a first recess may receive the user's thumb and a second recess may receive one or more of the user's fingers. The user may compress the adjacent walls of the recesses toward each other to grip the medical device between the first and second recesses.

Notably, the existence of a recess is optional. In some alternative embodiments (not shown), a retention feature may define an interior receptacle that can receive at least part of a medical device, but may not define a recess in which the user's hand is received. Rather, the receptacle may be defined by the interior of a boss or other projecting feature that can be grasped by hand. Such a projecting feature need not be positioned within a recess, but may instead protrude from the surrounding surface(s) of the packaging component of which it is a part.

Returning to the packaging assembly 100 of FIGS. 1 through 4, the first packaging component 120 may have a first end 140, a second end 142, a shoulder 144, and a retention feature 146. The first end 140 may be open toward the third packaging component 124 such that the first interior space 126 and the second interior space 128 are both accessible through the first end 140. The first interior space 126 and the second interior space 128 may both reside within the first packaging component 120. The first end 140 may define a flange 141 that facilitates sealed attachment of the cap 160 to the first packaging component 120, as will be described subsequently.

The second end 142 may be closed to keep the first interior space 126 separate from and sealed from the ambient space 129. The second end 142 may define a bottom surface 143 that may rest on a horizontal surface in such a manner that the packaging assembly 100 is stable and upright, maintaining the medical device 110 in a generally vertical orientation.

The shoulder 144 may have a generally annular shape that abuts a corresponding generally annular shape of the shoulder 134 of the second packaging component 122. This abutment may be a mechanical coupling only, such as a snug friction fit, or may include a seal, as discussed above. In some embodiments, the shoulder 134 and the shoulder 144 may optionally be bonded, welded, mechanically fastened, or otherwise secured together. In some embodiments, where the first packaging component 120 and the second packaging component 122 are both formed of plastic materials, ultrasonic welding or other polymer attachment methods may be used to secure the shoulder 134 to the shoulder 144, forming a mechanical attachment and/or a seal between the shoulder 134 and the shoulder 144. In alternative embodiments, any other form of attachment may be used, including but not limited to mechanical fastening (for example, threaded interconnection, bayonet fittings, clips, clasps, and the like), adhesive bonding, chemical bonding, and the like.

The retention feature 146 may be configured somewhat similarly to the retention feature 136 of the second packaging component 122, and may retain the second end 114 of the medical device 110 in a manner similar to retention of the first end 112 of the medical device 110 by the retention feature 136 of the second packaging component 122, as described previously. More precisely, the retention feature 146 may have a recess 148 with a generally annular shape that surrounds the second end 114, to define a first interior receptacle 149 that receives the second end 114. The recess 148 may optionally be large enough to accommodate fingertips, but in the alternative, the recess 148 maybe significantly smaller than the recess 138 of the second packaging component 122, as the operator need not grip the second end 114 of the medical device 110 through the first packaging component 120, but may instead simply grip the exterior of the second packaging component 122 as the first end 112 of the medical device 110 is gripped through the recess 138 (for example, with the operator's other hand) and pulled out of the first interior space 126. Thus, the retention feature 146 may simply provide retention force sufficient to retain the second end 114 of the medical device 110 against the second end 142 of the first packaging component 120 until the medical device 110 is to be removed from the packaging assembly 100. The retention feature 146 may help to keep the medical device 110 in a stable, upright orientation until it is to be used.

The third packaging component 124 may be generally disc-shaped, with a central expanse 154 and a rim 156, which may protrude from the central expanse 154 toward the first packaging component 120 and the second packaging component 122. The outer annular region of the central expanse 154 may abut the flange 141 of the first packaging component 120. In some embodiments, this outer annular region of the central expanse 154 may be attached and/or sealed to the flange 141. However, this optional; in some embodiments, the third packaging component 124 may not be sealed to any other component, and may instead act as a protective cap. As with attachment of the shoulder 134 to the shoulder 144, any known attachment technique may be used, such as welding, bonding, mechanical fastening, and/or the like. In embodiments in which the third packaging component 124 does not define a seal, it may provide a simple friction fit or the like with the first packaging component 120.

In some embodiments, the attachment of the central expanse 154 to the flange 141, and the attachment of the shoulder 134 to the shoulder 144, may be manually breakable (i.e., breakable by hand, without the need for tooling). Thus, a user may be able to open the packaging assembly 100 and withdraw the medical device 110 without the need for any particular tool.

The first packaging component 120, the second packaging component 122, and the third packaging component 124 may be formed of a variety of materials. The first packaging component 120, the second packaging component 122, and/or the third packaging component 124 may optionally be made of translucent or transparent materials to facilitate user recognition of the medical device 110, without needing to open the packaging assembly 100. In some embodiments, one or more polymers may be used. For example, the first packaging component 120, the second packaging component 122, and/or the third packaging component 124 may be composed of polyethylene terephthalate (PET), or any other materials known in the art suitable for use in sterilization processes.

Various components of the packaging assembly 100 may optionally be shaped to help prevent inadvertent non-sterile access to the first interior space 126. For example, the diameter of the second packaging component 122 may be large enough that a user gripping the second packaging component 122 via the recess 138 may be unable to move fingers of the gripping hand around the rim of the second packaging component 122, proximate the first end 130 of the second packaging component 122. Similarly, the first packaging component 120 may have a combination of length and diameter sufficient that a user gripping the first packaging component 120 via the recess 148 may be unable to move fingers of the gripping hand around the rim of the first packaging component 120, proximate the first end 140 of the first packaging component 120.

A user gripping the packaging assembly 100 to open the packaging assembly 100 need not have hands in a sterile condition. The user may be physically blocked from inserting potentially non-sterile digits into the first interior space 126. Thus, accidental contamination of the medical device 110 may be avoided.

Optionally, the packaging assembly 100 may have a protective insert 158 that holds the first end 112 of the medical device 110 within the second interior receptacle 139. The protective insert 158 may be a, rubber cap, or other member that covers the first end 112. The protective insert 158 may protect the first end 112 from damage during storage or use, or may protect other devices or individuals from harm that could otherwise be caused by the first end 112. For example, if the first end 112 has a sharp end, serrations, or other features that could cause harm or damage, the protective insert 158 may help prevent such harm or damage. It may be removed prior to or during surgical use of the medical device 110.

In addition or in the alternative to serving a protective function, the protective insert 158 may enhance the ability of the second interior receptacle 139 to securely grip the first end 112 of the medical device 110. The protective insert 158 is an optional feature; in some embodiments, it may be omitted in favor of direct retention of the first end 112 within the second interior receptacle 139. The protective insert is not shown in FIGS. 2, 3, and 4.

In the exemplary embodiment of FIGS. 1-4, the medical device 110 is stored such that the first end 112 of the medical device 110 is already retained in the second interior receptacle 139. In alternative embodiments (not shown), a medical device may be stored such that the portion of the medical device that is to be gripped through the packaging is not disposed within the receptacle that is to be used to grip and withdraw it. Rather, prior to withdrawing the medical device, the receptacle and/or the medical device may be maneuvered to insert the portion of the medical device into the receptacle, where it can be gripped by the packaging. In some embodiments, a portion of the packaging having the receptacle (for example, a lid) may be sized to be insertable into the interior space containing the medical device, so that it can be maneuvered by the user to reach into the packaging and grip the medical device.

In some embodiments, an assembly may have an interior receptacle that flexes to permit the user to selectively grip the medical device. For example, with reference to the packaging assembly 100 of FIGS. 1-4, the second interior receptacle 139 may be flexible so that the user can, in some configurations, grip the first end 112 of the medical device 110, and in other configurations, not grip the medical device 110. For example, the second interior receptacle 139 may have an undeflected shape in which the second interior receptacle 139 is significantly larger than the first end 112, so that the first end 112 is freely insertable into and removable from the second interior receptacle 139. The second interior receptacle 139 may further have a deflected shape that can be obtained by manually compressing the second interior receptacle 139 with fingers within the recess 138. In the deflected shape, the second interior receptacle 139 may fit more tightly around the first end 112, so that the first end 112 can be gripped in the second interior receptacle 139 until the user relaxes his or her grip on the second interior receptacle 139. Thus, the user may have the option to release the medical device 110 without having to actively pull it from the second interior receptacle 139 (for example, with a second hand). Such a variable-shaped receptacle may be particularly useful for configurations in which the medical device is not stored in the receptacle.

Returning to the embodiment of FIGS. 1-4, the packaging assembly 100 may be assembled in a variety of ways. The medical device 110 may first be inserted into the first interior space 126. The second end 114 of the medical device 110 may be inserted into the first interior receptacle 149 of the second packaging component 122. Then, the second packaging component 122 may be inserted through the first end 140 of the first packaging component 120, such that the first end 112 of the medical device 110 enters the second interior receptacle 139 of the second packaging component 122. The shoulder 134 may then be secured to the shoulder 144, optionally sealing the first interior space 126 such that the first interior space 126, and thus the medical device 110, is isolated from the ambient space 129.

In some embodiments, a cap 160 (shown in FIG. 3) may be used to provide a seal. The cap 160 may, for example, be secured to the flange 141 of the first packaging component 120 and may reside within the third packaging component 124 when the packaging assembly 100 is fully assembled. In some embodiments, the cap 160 may be secured to the flange 141 so as to form a seal that effectively isolates the first interior space 126 and the second interior space 128 from the ambient space 129. Any attachment method may be used, such as the ultrasonic welding, mechanical fastening, chemical bonding, and adhesive bonding techniques mentioned previously.

The third packaging component 124 may then be positioned such that the central expanse 154 abuts the cap 160. In some embodiments, a hermetic seal may be formed between the outer annular ring of the central expanse 154 and the flange 141 of the first packaging component 120. Such a seal may be used in addition to or in place of the seal provided between the cap 160 and the first packaging component 120. In alternative embodiments, only a single seal may be provided, such as the seal between the cap 160 and the first packaging component 120.

In other alternative embodiments, various components may be omitted. For example, in some embodiments, the third packaging component 124 may be omitted such that the cap 160 is exposed to the ambient space 129. In other embodiments, the third packaging component 124 and the cap 160 may both be omitted so that the exterior of the second packaging component 122 is exposed to the ambient space 129. In such an embodiment, a seal may be formed between the first packaging component 120 and the second packaging component 122, as described above.

In other embodiments, the cap 160 may be omitted, and the third packaging component 124 may remain. The first packaging component 120 and the second packaging component 122 may form a seal, or in some embodiments, may not form a seal. Rather, a seal may exist between the first packaging component 120 and the third packaging component 124. In still other embodiments, particularly where the cap 160 and/or the third packaging component 124 are omitted, in place of a seal between the first packaging component 120 and the third packaging component 124, a seal may exist between the second packaging component 122 and the third packaging component 124, which may be shaped to come into contact with each other (for example, at the rim of the second packaging component 122, proximate the first end 130 of the second packaging component 122) to define the seal.

In some embodiments, a single-seal embodiment as described above may contain an independently sealed package, with its own membrane. For example, a single-sealed assembly (not shown) as described above may contain a blister pack or other sealed package that, in turn, contains the medical device. Thus, the medical device may be doubly-sealed from the ambient space 129. In yet other alternative embodiments, a multi-sealed assembly may contain such a blister pack or other sealed package containing the medical device, providing three or more seals between the medical device and the ambient space 129.

Once the packaging assembly 100 has been assembled with the medical device 110 inside, the medical device 110 and the packaging assembly 100 may be sterilized. Any known sterilization methods, such as gamma sterilization, may be used. In alternative embodiments, rather than sterilizing the packaging assembly 100 and the medical device 110 after assembly, the medical device 110 and the packaging assembly 100 may instead be sterilized prior to assembly, and assembled in a sterile environment.

The packaging assembly 100 and the medical device 110 may be used in a variety of ways. According to one way, the operator may first grip the rim 156 of the third packaging component 124 and pull the rim 156 away from the first packaging component 120, removing the third packaging component 124 from the second packaging component 122. If the third packaging component 124 is not part of the seal and is not secured to the cap 160, the cap 160 may then be removed from the flange 141, opening the seal.

Then, the operator may grip the first packaging component 120 with one hand, and insert the fingertips of the other hand into the second interior receptacle 139 of the second packaging component 122 to grip the first end 112 of the medical device 110 through the recess 138 of the second packaging component 122, as shown in FIG. 4. While gripping the first end 112 through the recess 138, the operator may pull the first end 112 out of the first interior space 126. The operator may then insert the medical device 110 directly into the sterile field, avoiding the need for the user to contact the medical device 110 with his or her hands or gloves.

Figure 5A:
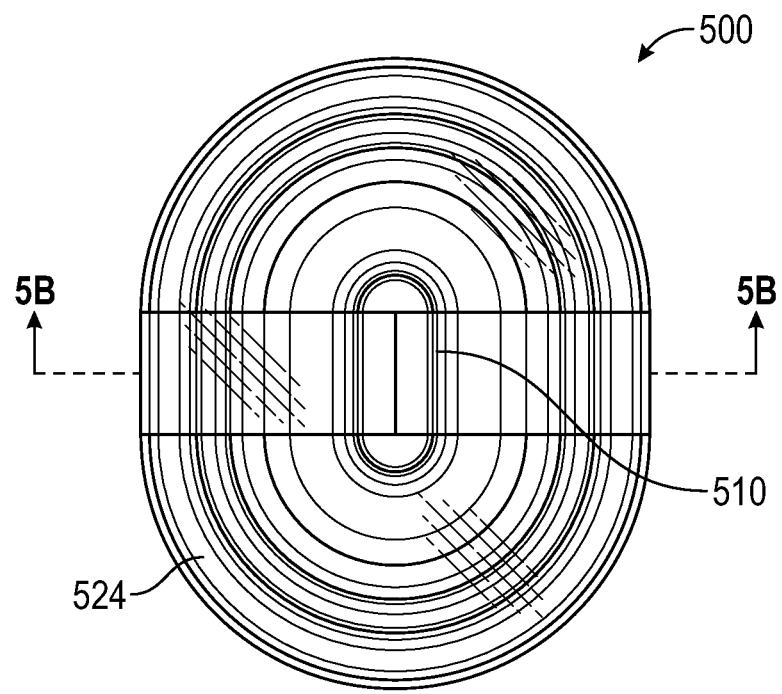
FIGS. 5A, 5B, and 5C are a plan view, side elevation view, and a perspective view, respectively, of a packaging assembly according to one alternative embodiment.
Figure 5B:
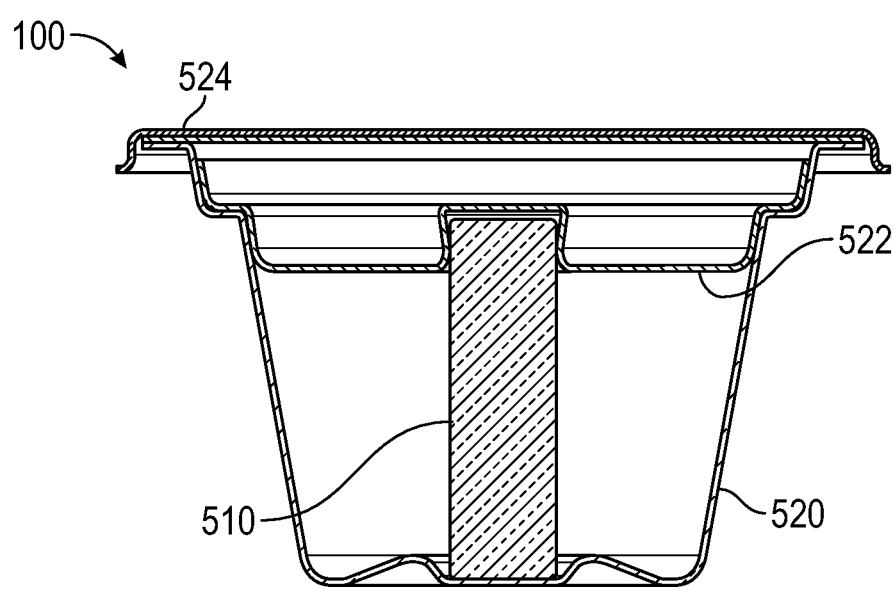
Figure 5C:
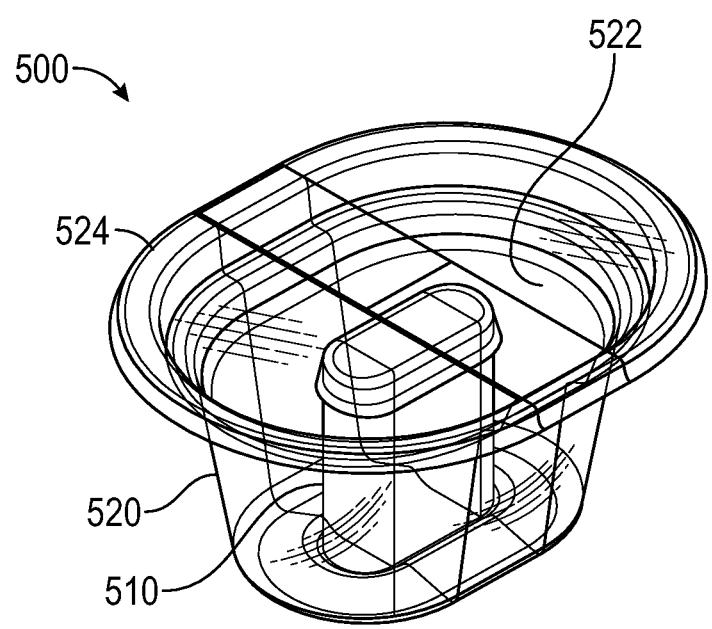

As indicated previously, packaging assemblies of a wide variety of shapes and sizes may be used. FIGS. 5A, 5B, and 5C are plan, side elevation, and perspective views of an assembly 500 according to one alternative embodiment. The packaging assembly 500 may be used to store a medical device 510 with an elongated (non-cylindrical) cross-sectional shape. In order to accommodate the shape of the medical device 510, the packaging assembly 500 may have a first packaging component 520, a second packaging component 522, and a third packaging component 524 that all have a similarly elongated shape. These components may not be radially symmetrical like their counterparts of the packaging assembly 100 but may instead have extra length in the vertical direction of FIG. 5A to accommodate the shape of the medical device 510.

Other shapes may be used in other alternative embodiments (not shown). For example, some assemblies may have the shape of a rectangular prism, a triangular prism, a pyramid, a cone, a frustoconical shape, and/or the like. Those of skill in the art will recognize that the packaging assembly 100, the packaging assembly 500, and the alternatives described above represent just a small sample of many possible assembly shapes that may be used within the scope of the present disclosure. Many other shapes may be used to store medical devices of various shapes and sizes.

In some alternative embodiments (not shown), multiple medical devices (for example, multiple sizes of a single implant or instrument type, or multiple implants and/or instruments intended to be used together) may be stored and sealed together in a single packaging assembly. Some packaging assemblies may have multiple distinct, and optionally sealed, interior spaces, each containing one or more medical devices. Such interior spaces may be independently opened to unseal and use one or more medical devices, leaving the remainder in a sealed condition. Numerous modifications may be made to suit various medical devices, procedures, and/or operating environments.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this description are hereby expressly incorporated into this description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. A packaging assembly for retaining a medical device, the packaging assembly comprising:
    a first packaging component; and
    a second packaging component;
    wherein the first packaging component and the second packaging component are attachable to each other to define a first interior space containing the medical device, wherein the first interior space is hermetically sealed from ambient space;
    wherein the first packaging component comprises a first retention feature that defines a first interior receptacle shaped to receive at least part of the medical device;
    wherein the first interior receptacle is sufficiently flexible that a user can manually grip the medical device by compressing the first interior receptacle against the medical device.

2. The packaging assembly of claim 1, wherein the first retention feature further defines a first recess proximate the medical device, wherein the first recess is shaped to receive at least part of a user's hand.

3. The packaging assembly of claim 2, wherein:
    the medical device comprises a first medical device end and a second medical device end;
    the first recess comprises a substantially annular shape that defines the first interior receptacle; and
    the first interior receptacle is shaped to receive the first medical device end.

4. The packaging assembly of claim 3, wherein the second packaging component comprises a second retention feature that defines a second interior receptacle that receives the second medical device end.

5. The packaging assembly of claim 1, wherein:
    the medical device comprises a first medical device end and a second medical device end; and
    the second packaging component comprises a first end at which the second packaging component is secured to the first packaging component, and a second end defining a base capable of supporting the packaging assembly in an upright orientation, with the first packaging component over the second packaging component, and the medical device upright with the first medical device end over the second medical device end.

6. The packaging assembly of claim 1, wherein the first packaging component is detachable from the second packaging component in response to manual exertion of a detachment force exerted by a user gripping the medical device through the first retention feature.

7. The packaging assembly of claim 1, further comprising a third packaging component securable to the second packaging component to define a second interior space between the first interior space and an ambient space outside the packaging assembly.

8. The packaging assembly of claim 1, further comprising a cap securable to the first packaging component to define a seal that seals the first interior space from ambient space.

9. The packaging assembly of claim 1, wherein:
the medical device comprises a first medical device end and a second medical device end;
the second packaging component comprises a second retention feature that defines a second interior receptacle; and
with the first packaging component and the second packaging component attached to each other to define the first interior space, the first medical device end resides in the first interior receptacle and the second medical device end resides in the second interior receptacle.

10. The packaging assembly of claim 1, wherein the first interior receptacle comprises:
an undeflected shape in which the part of the medical device is freely removable from the first interior receptacle; and
a deflected shape in which the first interior receptacle fits more tightly around the part of the medical device.

11. The packaging assembly of claim 1, wherein the first interior receptacle comprises:
a proximal end further from the second packaging component; and
a distal end nearer the second packaging component;
wherein the proximal end is larger than the distal end.

12. The packaging assembly of claim 11, wherein:
the distal end is sized to fit tightly around the part of the medical device; and
the proximal end is sized to receive the part of the medical device with clearance.

13. The packaging assembly of claim 1, wherein the first packaging component and the second packaging component are made of plastic materials.

14. A system comprising:
a medical device comprising an implant or instrument, the medical device comprising:
a first medical device end; and
a second medical device end; and
a packaging assembly comprising:
a first packaging component comprising a first retention feature that defines:
a first interior receptacle in which the first medical device end resides; and
a recess sized to receive at least part of a hand of a user and sufficiently flexible to permit the user to compress the first interior receptacle against the first medical device end;
a second packaging component comprising a second retention feature that defines a second interior receptacle in which the second medical device end resides;
wherein the first packaging component and the second packaging component are attachable to each other to define a first interior space containing the medical device in a sealed condition.

15. The system of claim 14, further comprising a third packaging component securable to the second packaging component to define a second interior space between the first interior space and an ambient space outside the packaging assembly.

16. The system of claim 14, wherein the first packaging component is detachable from the second packaging component in response to manual exertion of a detachment force exerted by a user gripping the medical device through the first retention feature.

17. The packaging assembly of claim 14, wherein the first interior receptacle comprises:
an undeflected shape in which the first medical device end is freely removable from the first interior receptacle; and
a deflected shape in which the first interior receptacle fits more tightly around the first medical device end.

18. The packaging assembly of claim 14, wherein the first interior receptacle comprises:
a proximal end further from the second packaging component; and
a distal end nearer the second packaging component;
wherein the proximal end is larger than the distal end.

19. The packaging assembly of claim 18, wherein:
the distal end is sized to fit tightly around the first medical device end; and
the proximal end is sized to receive the first medical device end with clearance.

20. The packaging assembly of claim 14, wherein the first packaging component and the second packaging component are made of plastic materials.

21. A packaging assembly for retaining a medical device, the packaging assembly comprising:
a first packaging component; and
a second packaging component;
wherein the first packaging component and the second packaging component are attachable to each other to define a first interior space containing the medical device, wherein the first interior space is sealed from ambient space;
wherein the first packaging component comprises:
a first recess; and
a first retention feature, proximate the first recess, that defines a first interior receptacle shaped to receive at least part of the medical device;
wherein the first interior receptacle is sufficiently flexible that a user can manually grip the medical device through the first recess by compressing the first interior receptacle against the medical device.

22. The packaging assembly of claim 21, wherein:
the medical device comprises a first medical device end and a second medical device end;
the first recess comprises a substantially annular shape that defines the first interior receptacle; and
the first interior receptacle is shaped to receive the first medical device end.

23. The packaging assembly of claim 22, wherein the second packaging component comprises a second retention feature that defines a second interior receptacle that receives the second medical device end.

24. The packaging assembly of claim 21, wherein the first packaging component is detachable from the second packaging component in response to manual exertion of a detachment force exerted by a user gripping the medical device through the first retention feature.

* * * * *